(12) United States Patent
Rothblatt

(10) Patent No.: US 12,636,288 B2
(45) Date of Patent: May 26, 2026

(54) METHODS AND COMPOSITIONS FOR TREATING PULMONARY HYPERTENSION

(71) Applicant: United Therapeutics Corporation, Silver Spring, MD (US)

(72) Inventor: Martine A. Rothblatt, Silver Spring, MD (US)

(73) Assignee: United Therapeutics Corporation, Silver Spring, MD (US)

( * ) Notice: Subject to any disclaimer, the term of this patent is extended or adjusted under 35 U.S.C. 154(b) by 275 days.

(21) Appl. No.: 16/831,399

(22) Filed: Mar. 26, 2020

(65) Prior Publication Data

US 2020/0222412 A1 Jul. 16, 2020

Related U.S. Application Data

(63) Continuation of application No. 15/865,948, filed on Jan. 9, 2018, now abandoned.

(60) Provisional application No. 62/444,547, filed on Jan. 10, 2017.

(51) Int. Cl.
| | |
|---|---|
| *A61K 31/53* | (2006.01) |
| *A61K 9/00* | (2006.01) |
| *A61K 33/00* | (2006.01) |
| *A61K 45/06* | (2006.01) |
| *A61P 9/12* | (2006.01) |

(52) U.S. Cl.
CPC ............ *A61K 31/53* (2013.01); *A61K 9/0075* (2013.01); *A61K 9/0078* (2013.01); *A61K 33/00* (2013.01); *A61K 45/06* (2013.01); *A61P 9/12* (2018.01); *A61K 9/008* (2013.01); *A61K 2300/00* (2013.01)

(58) Field of Classification Search
CPC ....................................................... A61P 9/12
See application file for complete search history.

(56) References Cited

U.S. PATENT DOCUMENTS

| | | | |
|---|---|---|---|
| 4,954,526 A | 9/1990 | Keefer | |
| 5,155,137 A | 10/1992 | Keefer et al. | |
| 5,427,797 A | 6/1995 | Frostell et al. | |
| 5,840,759 A | 11/1998 | Mitchell et al. | |
| 8,927,030 B2 | 1/2015 | Gladwin et al. | |
| 9,387,224 B2 | 7/2016 | Gladwin et al. | |
| 2009/0196930 A1* | 8/2009 | Surber | A61P 9/12 |
| | | | 128/203.15 |
| 2020/0093830 A1* | 3/2020 | Weers | A61K 9/008 |

FOREIGN PATENT DOCUMENTS

| | | |
|---|---|---|
| WO | WO 92/17445 A2 | 10/1992 |
| WO | WO 95/09612 A1 | 4/1995 |
| WO | WO 2009/086470 A2 | 7/2009 |
| WO | WO 2009/115235 A1 | 9/2009 |

OTHER PUBLICATIONS

Pharmacokinetics, Pharmacodynamics, Safety, and Tolerability of Nebulized Sodium Nitrite (AIR001) Following Repeat-Dose Inhalation in Healthy Subjects Rix et al. Clin Pharmacokinet (2015) 54:261-272 (Year: 2014).*
Vardenafil: structural basis for higher potency over sildenafil in inhibiting cGMP-specific phosphodiesterase-5 (PDE5) Corbin et al. Neurochemistry International 45 (2004) 859-863 (Year: 2004).*
Ari, Zrxu "Jet, Ultrasonic, and Mesh Nebulizers: An Evaluation of Nebulizers for Better Clinical Outcomes," Eurasian Journal of Pulmonology, 2014; 16: 1-7.
Berry et al. "Comparison of Pharmacokinetics of Vardenafil Administered Using an Ultrasonic Nebulizer for Inhalation vs a Single 10mg Oral Tablet," J. Sex. Med., Jul. 2016, 13(7):1111-1118. doi: 10.1111/j.17436109.2009.01403.
Dias-Junior et al., "Sildenafil Improves the Beneficial Haemodynamic Effects of Intravenous Nitrite Infusion during Acute Pulmonary Embolism," Basic & Clinical Pharmacology & Toxicology, Sep. 16, 2008, 103(4):374-379.
Dworetz et al., "Survival of Infants With persistent Pulmonary Hypertension Without Extracorporeal Membrane Oxygenation," Pediatrics, 1989, 84(1):1-6.
Fox et al., "Pulmonary Hypertension in the Perinatal Aspiration Syndromes," Pediatrics, 1977, 59(2):205-211.
Peckham et al., "Physiologic factors affecting pulmonary artery pressure in infants with persistent pulmonary hypertension," J. Pediatrics, 1978, 93(6):1005-1010.
Simon et al., "Acute hemodynamic effects of inhaled sodium nitrite in pulmonary hypertension associated with heart failure with preserved ejection fraction," JCI Insight, Nov. 3, 2016, 1(18):e89620, 1-13.
Simonneau et al., "Clinical Classification of Pulmonary Hypertension," J. Am. Coll. Cardiol., 2004; 43(12 Suppl S):5S-12S.
Zapol et al., "Pulmonary Circulation During Adult Respiratory Distress Syndrome," Pulmonary Cicculation During ARDS, 1985, 241-273.

* cited by examiner

*Primary Examiner* — Jeffrey S Lundgren
*Assistant Examiner* — Eric Tran
(74) *Attorney, Agent, or Firm* — Foley & Lardner LLP

(57) ABSTRACT

The present disclosure provides compositions and methods for treating pulmonary hypertension. The compositions and methods are based on administering a NO-releasing compound, such as nitrite, to a subject in need thereof in an amount sufficient to increase the level of circulating nitric oxide (NO), a potent vasodilator, thereby reducing the subject's blood pressure and increasing blood flow.

18 Claims, No Drawings

METHODS AND COMPOSITIONS FOR TREATING PULMONARY HYPERTENSION

CROSS-REFERENCE TO RELATED APPLICATIONS

This application is a Continuation of U.S. application Ser. No. 15/865,948, filed Jan. 9, 2018, which claims priority to U.S. Provisional Application No. 62/444,547, filed Jan. 10, 2017.

TECHNICAL FIELD

The present invention relates to compositions and methods for treating pulmonary hypertension based on administering to a subject in need thereof a nitric oxide (NO)-releasing compound and a phosphodiesterase type-5 (PDE5) inhibitor.

BACKGROUND

All blood is driven through the lungs via the pulmonary circulation in order, among other things, to replenish the oxygen which it dispenses in its passage around the rest of the body via the systemic circulation. The flow through both circulations is in normal circumstances equal, but the resistance offered to it in the pulmonary circulation is generally much less than that of the systemic circulation. When the resistance to pulmonary blood flow increases, the pressure in the circulation is greater for any particular flow. The above described condition is referred to as pulmonary hypertension (PH). Generally, pulmonary hypertension is defined through observations of pressures above the normal range pertaining in the majority of people residing at the same altitude and engaged in similar activities.

Pulmonary hypertension may occur due to various reasons and the different entities of pulmonary hypertension were classified based on clinical and pathological grounds in 5 categories according to the latest WHO convention, see e.g. Simonneau G., et al. J. Am. Coll. Cardiol. 2004; 43(12 Suppl S):5S-12S. Pulmonary hypertension can be a manifestation of an obvious or explicable increase in resistance, such as obstruction to blood flow by pulmonary emboli, malfunction of the heart's valves or muscle in handling blood after its passage through the lungs, diminution in pulmonary vessel caliber as a reflex response to alveolar hypoxia due to lung diseases or high altitude, or a mismatch of vascular capacity and essential blood flow, such as shunting of blood in congenital abnormalities or surgical removal of lung tissue. In addition, certain infectious diseases, such as HIV and liver diseases with portal hypertension may cause pulmonary hypertension. Autoimmune disorders, such as collagen vascular diseases, also often lead to pulmonary vascular narrowing and contribute to a significant number of pulmonary hypertension patients. The cases of pulmonary hypertension remain where the cause of the increased resistance is as yet inexplicable are defined as idiopathic (primary) pulmonary hypertension (iPAH) and are diagnosed by and after exclusion of the causes of secondary pulmonary hypertension and are in the majority of cases related to a genetic mutation in the bone morphogenetic protein receptor-2 gene. The cases of idiopathic pulmonary arterial hypertension tend to comprise a recognizable entity of about 40% of patients cared for in large specialized pulmonary hypertension centers. Approximately 65% of the most commonly afflicted are female and young adults, though it has occurred in children and patients over 50. Life expectancy from the time of diagnosis is short without specific treatment, about 3 to 5 years, though occasional reports of spontaneous remission and longer survival are to be expected given the nature of the diagnostic process. Generally, however, disease progress is inexorable via syncope and right heart failure and death is quite often sudden.

Pulmonary hypertension refers to a condition associated with an elevation of pulmonary arterial pressure (PAP) over normal levels. In humans, a typical mean PAP is approximately 12-15 mm Hg. Pulmonary hypertension, on the other hand, can be defined as mean PAP above 25 mmHg, assessed by right heart catheter measurement. Pulmonary arterial pressure may reach systemic pressure levels or even exceed these in severe forms of pulmonary hypertension. When the PAP markedly increases due to pulmonary venous congestion, such as in left heart failure or valve dysfunction, plasma can escape from the capillaries into the lung interstitium and alveoli. Fluid buildup in the lung (pulmonary edema) can result, with an associated decrease in lung function that can in some cases be fatal. Pulmonary edema, however, is not a feature of even severe pulmonary hypertension due to pulmonary vascular changes in all other entities of this disease.

Pulmonary hypertension may either be acute or chronic. Acute pulmonary hypertension is often a potentially reversible phenomenon generally attributable to constriction of the smooth muscle of the pulmonary blood vessels, which may be triggered by such conditions as hypoxia (as in high-altitude sickness), acidosis, inflammation, or pulmonary embolism. Chronic pulmonary hypertension is characterized by major structural changes in the pulmonary vasculature, which result in a decreased cross-sectional area of the pulmonary blood vessels. This may be caused by, for example, chronic hypoxia, thromboembolism, collagen vascular diseases, pulmonary hypercirculation due to left-to-right shunt, HIV infection, portal hypertension or a combination of genetic mutation and unknown causes as in idiopathic pulmonary arterial hypertension.

Pulmonary hypertension has been implicated in several life-threatening clinical conditions, such as adult respiratory distress syndrome ("ARDS") and persistent pulmonary hypertension of the newborn ("PPHN"). Zapol et al., Acute Respiratory Failure, p. 241-273, Marcel Dekker, New York (1985); Peckham, J. Ped. 93:1005 (1978). PPHN, a disorder that primarily affects full-term infants, is characterized by elevated pulmonary vascular resistance, pulmonary arterial hypertension, and right-to-left shunting of blood through the patent ductus arteriosus and foramen ovale of the newborn's heart. Mortality rates range from 12-50%. Fox, Pediatrics 59:205 (1977); Dworetz, Pediatrics 84:1 (1989). Pulmonary hypertension may also ultimately result in a potentially fatal heart condition known as "cor pulmonale," or pulmonary heart disease. Fishman, "Pulmonary Diseases and Disorders" 2nd Ed., McGraw-Hill, New York (1988).

SUMMARY OF THE INVENTION

One embodiment is a method for treating pulmonary hypertension comprising administering to a subject suffering from pulmonary hypertension a therapeutically effective amount of a PDE-5 inhibitor and an NO-releasing compound. In some embodiments, the PDE5 inhibitor is vardenafil or a pharmaceutically acceptable salt or ester thereof, such as vardenafil HCl. In some embodiments, the NO-releasing compound is a pharmaceutically acceptable nitrite, such as sodium nitrite. In some embodiments, the subject being treated is suffering from neonatal pulmonary hypertension, primary pulmonary hypertension and/or secondary pulmonary hypertension.

In some embodiments, the present methods can be used, alone or in combination with other therapies, for the treatment or improvement of various conditions associated with an elevated blood pressure, such as by decreasing the blood pressure, increasing the blood flow to a tissue, and/or inducing vasodilation in a subject. Particularly, in some embodiments, the present methods achieve the desired effect through the in vivo production of a sufficient amount of nitric oxide (NO) in the subject.

Further in some embodiments, the present methods can extend the half-life or reduce the in vivo elimination rate of a NO-releasing compound following its administration to a subject. In some embodiments, the method comprises co-administering the NO-releasing compound with at least one PDE5 inhibitor, thereby preventing premature breakdown of the NO-releasing compound or delaying breakdown of the NO-releasing compound. In various embodiments, the PDE5 inhibitor and the NO-releasing compound may be administered simultaneously or sequentially. Particularly, in some embodiments, the PDE5 inhibitor and the NO-releasing compound are co-administered, such that their respective effective periods of biological activity will overlap upon administration to the subject. In some embodiments, the amount of the PDE5 inhibitor is sufficient to improve bioavailability of nitric oxide (NO) by extending the half-life or reducing the elimination rate of the administered NO-releasing compound in the subject.

In some embodiments, at least one of the PDE5 inhibitor and the NO-releasing compound are administered by inhalation. In some embodiments, a single pharmaceutical composition comprising the PDE5 inhibitor and the NO-releasing compound is administered by inhalation to the subject. Particularly, in some embodiments, the pharmaceutical composition is nebulized, such as converting into a liquid or dry powder aerosol for inhalation by the subject. Particularly, in some embodiments, the present methods use a metered dose inhaler for administration, such as a pulsed inhaler that aerosolizes a fixed amount of the formulation per pulse, a dry powder inhaler or a soft mist inhaler.

In another aspect of the present disclosure, provided herein are pharmaceutical compositions for treating pulmonary hypertension. The compositions comprise at least one PDE5 inhibitor and at least one NO-releasing compound. In some embodiments, the PDE5 inhibitor is vardenafil or a pharmaceutically acceptable salt or ester thereof, such as vardenafil HCl. In some embodiments, the NO-releasing compound is a pharmaceutically acceptable nitrite, such as sodium nitrite. In some embodiments, the composition may be used to treat a subject suffering from neonatal pulmonary hypertension, primary pulmonary hypertension and/or secondary pulmonary hypertension.

In some embodiments, the composition is formulated for delivery by inhalation. For example, in some embodiments, the composition is in the form of an aerosol or another form to be nebulized into an aerosol before administration. Particularly, the aerosol exhibits various properties favorable for depositing the drug-containing droplets or particles in a subject's lung, thereby maximize the effect in treating pulmonary hypertension. In some embodiments, the aerosol exhibits a mass median aerodynamic diameter (MMAD) of droplets or particles in the range of about 1 to about 10 μm. In some embodiments, the aerosol exhibits a geometric standard deviation (GSD) of less than 5. In some embodiments, the aerosol contains at least about 50% particles or droplets of less than about 5 μm in diameter.

In yet another aspect of the present disclosure, provided herein are kits for treating a pulmonary hypertension condition. In some embodiments, the kit comprises (i) a metered dose inhaler containing a pharmaceutical composition comprising at least one PDE5 and at least one NO-releasing compound; and (ii) instructions for use of in treating pulmonary hypertension. In some embodiments, the kit comprises (i) a first effective amount of a PDE5 inhibitor; (ii) a second effective amount of a NO-releasing compound; (iii) a metered dose inhaler; and (iv) instructions for use in treating pulmonary hypertension. In some embodiments, the PDE5 inhibitor is vardenafil or a pharmaceutically acceptable salt or ester thereof, such as vardenafil HCl. In some embodiments, the NO-releasing compound is a pharmaceutically acceptable nitrite, such as sodium nitrite. In some embodiments, the composition may be used to treat a subject suffering from neonatal pulmonary hypertension, primary pulmonary hypertension and/or secondary pulmonary hypertension.

DETAILED DESCRIPTION

Unless otherwise specified, "a" or "an" means "one or more." In one aspect, provided herein are methods for treating a subject suffering from a condition associated with an elevated blood pressure. The term "subject" as used herein refers to living multi-cellular organisms, including vertebrate organisms, a category that include both human and non-human mammals. The methods and compositions as disclosed herein have equal application in medical and veterinary settings. Thus, the general term "subject" under the treatment is understood to include all animals, such as humans, domestic animals, wild animals and laboratory animals.

The term "treating" or "treatment" covers the treatment of a disease or disorder described herein, in a subject, such as a human, and includes: (i) inhibiting a disease or disorder, e.g., arresting its development; (ii) relieving a disease or disorder, e.g., causing regression of the disorder; (iii) slowing progression of the disorder; and/or (iv) inhibiting, relieving, or slowing progression of one or more symptoms of the disease or disorder. For example, treatment of a condition associated with an elevated blood pressure includes but is not limited to, preventing or ameliorating elevation of blood pressure in a subject's pulmonary circulation and/or systemic circulation above the normal range, as well as ensuing symptoms and complications.

Without being bound by theory, treatment of a condition associated with an elevated blood pressure may be achieved through maintaining within normal ranges one or more of right atrial pressure, pulmonary capillary wedge pressure, right ventricular systolic and diastolic pressures, pulmonary artery systolic and diastolic pressures, pulmonary artery compliance and pulmonary vascular resistance in the subject. Particularly, the treatment can include increasing blood flow in the subject through the induction of vasodilation or the prevention of vasoconstriction in the subject, etc.

The term "vasoconstriction" refers to the diminution of the caliber or cross-sectional area of a blood vessel, for example constriction of arterioles leading to decreased blood flow to a body part or tissue. Vasoconstriction can be induced by specific agents or drugs that cause directly or indirectly, constriction of blood vessels. Such an agent can be referred to as a vasoconstrictor. Vasoconstriction can also result from vasospasm, inadequate vasodilation, thickening of vessel walls, or the accumulation of flow-restricting material on the internal wall surfaces or within the wall.

The term "vasodilation" refers to a state of increased caliber of the blood vessels, or the act of dilation of a blood vessel, for instance dilation of arterioles leading to increased blood flow to a body part. This can be caused by a specific agent that causes, directly or indirectly, dilation of blood vessels. Such an agent can be referred to as a vasodilator. For example, it has been shown that nitric oxide (NO) is a potent dilator.

Particularly, contemplated herein are methods and compositions for treating or preventing a condition in a subject associated with elevated blood pressure in the lungs, such as pulmonary hypertension. In some embodiment, this includes treating a subject suffering from neonatal pulmonary hypertension. In other embodiments, this includes treating a subject suffering from primary and/or secondary pulmonary hypertension. In some embodiments, this includes treating a subject suffering from pulmonary arterial hypertension. The "pulmonary hypertension" treated can be one or more of the WHO classifications for pulmonary hypertension: Group 1 (pulmonary arterial hypertension); Group 1' (pulmonary veno-occlusive disease (PVOD) and/or pulmonary capillary haemangiomatosis (PCH)); Group 2 (Pulmonary hypertension due to left heart diseases); Group 3 (pulmonary hypertension due to lung diseases and/or hypoxemia); Group 4 (chronic thromboembolic pulmonary hypertension (CTEPH)); Group 5 (pulmonary hypertension with unclear multifactorial mechanisms). For example, "pulmonary hypertension" can refer to any of Group 1-5 pulmonary hypertension or any combination of those groups.

Also contemplated herein are methods and compositions for treating or preventing other conditions associated with elevated blood pressure or decreased blood flow, including vasospasm, stroke, angina, ischemia, revascularization of coronary arteries and other arteries (peripheral vascular disease), transplantation (e.g., of kidney, heart, lung, or liver), treatment of low blood pressure (such as that seen in shock or trauma, surgery and cardiopulmonary arrest) to prevent reperfusion injury to vital organs, cutaneous ulcers (e.g., with topical, non-acidified nitrite salt), Reynaud's phenomenon, treatment of hemolytic conditions (such as sickle cell, malaria, TTP, and HUS), hemolysis caused by immune incompatibility before and after birth, and other conditions.

Treatment of diseases in a subject can be through the administration suitable pharmaceutical agent(s) or drugs to the subject suffering from the disease or a condition or symptom associated with the disease.

A "pharmaceutical agent" or "drug" as used herein refers to a chemical compound or other composition capable of inducing a desired therapeutic or prophylactic effect when properly administered to a subject. In some embodiments, a pharmaceutical agent or drug may be administered as a prodrug, substrate or precursor, which terms refer to a compound that, after administration, is metabolized (i.e., converted within the body) into a pharmacologically active agent. For example, a prodrug, substrate or precursor may be used to improve absorption, distribution, metabolism and/or excretion (ADME scheme) of the corresponding drug, thus improving pharmacodynamics, such as bioavailability, of the corresponding drug.

Particularly, in some embodiments, the present methods comprise administering to a subject suffering from pulmonary hypertension a therapeutically effective amount of at least one PDE5 inhibitor and at least one NO-releasing compound.

The term "Phosphodiesterase Type-5 inhibitor" or "PDE5 inhibitor" as used herein refers to compounds or molecules capable of blocking the degradative action of cGMP specific PDE5 on cyclic GMP in the smooth muscle cells lining arterial walls. The phosphodiesterase inhibitor used in the methods disclosed herein can be any type of PDE5 inhibitor, or an analogue that is known in the art. By way of non-limiting example, some PDE5 inhibitors that are contemplated for use in connection with the present invention include sildenafil, tadalafil, vardenafil, avanafil, zaprinast, dipyridamole, 3-isobutyl-1-methylxanthine (IBMX), propentofylline, papaverine, 4-bromo-5-(pryidylmethylamino)-6-[3-(4-chlorophenyl)propxy]-3(2H)pyridazi-none, 1-[4-[(1,3-benzodiozol-5-9pyridylmethylamino)-6-chloro-2-quinazoliny-1]-4-piperidine-carboxylic acid, (+)-cis-5,6a,7,9,9,9a-hexahydro-2-[4-(trifloromethyl)-phenylmethyl-5-meth-yl cyclopent-4,5]imidazo[2.1-b]purin-4(3H)one, furazlocillin, cis-2-hexyl-5-methyl 3,4,5,6a,7,8,9,9a-octahy-drocyclopent[4,5]imidazo[2,1-b]purin-4-one, 3-acetyl-1-(2-chlorobenzyl)-2-propylindole-6-carboxylate, 4-bromo-5-(3-pyridylmethylamino)-6-(3-(4-chlorophenyl) propoxy)-3 (2H)pyridazinone, 1-methyl-5-(5morpholinoacetyl-2-n-propoxyphenyl)-3-n-propyl-1,6-dihydro-7H-pyrazolo(4,3-d)pyrimidin-7-one, 1-[4[(1,3-benzyodioxol-5-methyl) amino]-6-chloro-2-quinazolinyl]4-piperidine carboxylic acid, an analogue of any thereof, combinations thereof, or pharmaceutically acceptable salt, N-oxide, ester, quaternary ammonium salt, hydrate or prodrug thereof.

Particularly, in some embodiments, the PDE5 inhibitor is vardenafil, or a pharmaceutically acceptable salt or ester of vardenafil. It has been found that vardenafil may be safely administered via the inhaled route of administration with improved pharmacokinetics. Pharmacokinetics in human subjects of vardenafil administered by inhalation can be found in Berry et al. "Comparison of Pharmacokinetics of Vardenafil Administered Using an Ultrasonic Nebulizer for Inhalation vs a Single 10 mg Oral Tablet," J Sex Med. 2016 July; 13(7):11118. doi: 10.1111/j.17436109.2009.01403, which reference is herein incorporated by reference in its entirety.

The term "pharmaceutically acceptable" as used herein refers to safe and sufficiently non-toxic for administration to a subject. By way of non-limiting example, some pharmaceutically acceptable vardenafil salt or ester that are contemplated for use in connection with the present invention include those formed with an inorganic base, organic base, inorganic acid, organic acid, or basic or acidic amino acid. Salts of inorganic bases can be, for example, salts of alkali metals such as sodium or potassium; alkaline earth metals such as calcium and magnesium or aluminum; and ammonia. Salts of organic bases can be, for example, salts trimethylamine, triethylamine, pyridine, picoline, ethanolamine, diethanolamine, and triethanolamine. Salts of inorganic acids can be, for example, salts of hydrochloric acid, hydroboric acid, nitric acid, sulfuric acid, and phosphoric acid. Salts of organic acids can be, for example, salts of formic acid, acetic acid, trifluoroacetic acid, fumaric acid, oxalic acid, lactic acid, tartaric acid, maleic acid, citric acid, succinic acid, malic acid, methanesulfonic acid, benzene-sulfonic acid, and p-toluenesulfonic acid. Salts of basic amino acids can be, for example, salts of arginine, lysine and ornithine. Salts of acidic amino acids can include, for example, salts of aspartic acid and glutamic acid. Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides.

More particularly, in some embodiments, the PDE5 inhibitor is vardenafil hydrochloride.

Nitric oxide (NO) has a critical biological role as a potent vasodilator, contributing to the regulation of blood flow and cardiovascular hemostasis. The terms "nitric oxide (NO)-releasing compound," "NO-donor" and "NO-upregulators" may be used interchangeably to refer to nitrogen (N)-containing compounds that are capable of producing nitric oxide under physiological conditions, thereby upregulating nitric oxide availability in vivo. For simplicity, NO-releasing compounds, NO-donor and NO-upregulators will be referred to only as "NO-releasing compounds" in this application. Known NO-releasing compounds useful in the present invention include, but are not limited to: nitroso or nitrosyl compounds characterized by an —NO moiety that is spontaneously released or otherwise transferred from the compound under physiological conditions (e.g. S-nitroso-N-acetylpenicillamine, S-nitroso-L-cysteine, nitrosoguanidine, S-nitrosothiol, and others described in WO 92/17445 and U.S. Pat. No. 5,427,797 (herein incorporated by reference in its entirety). In addition, other NO-releasing compounds include compounds in which NO is a ligand on a transition metal complex, and as such is readily released or transferred from the compound under physiological conditions (e.g. nitroprusside, NO-ferredoxin, NO-heme complex) and nitrogen-containing compounds which are metabolized by enzymes endogenous to the respiratory and/or vascular system to produce the NO radical (e.g. arginine, glyceryl trinitrate, isoamyl nitrite, inorganic nitrite, azide and hydroxylamine). More NO-releasing compounds are polyethyleneimine (PEI)-based polymers exposed to NO gas; molsidomine; nitrate esters; sodium nitrite; iso-sorbide didinitrate; penta erythritol tetranitrate; nitroimidazoles; complexes of nitric oxide and polyamines; anionic diazeniumdiolates (NONOates) (including those disclosed in U.S. Pat. Nos. 4,954,526 and 5,155,137) and the NO releasing compounds disclosed in U.S. Pat. No. 5,840,759 and PCT WO 95/09612. Examples of NONOate compounds include diethylamine/NONO, diethylenetriamine/NONO, and methylaminohexylmethylamine/NONO (illustrated in Hanson et al., Nitric Oxide, Biochemistry, Molecular Biology, and Therapeutic Implications, Ignarro and Murad, Ed., Academic Press, New York (1995)). An NO-releasing compound, donor or upregulator can be provided in powder form or as a liquid (e.g., by mixing the compound with a biologically-compatible excipient). The NO-releasing compound can be administered to the patient alone or in conjunction with NO gas, CO gas, a carrier gas or another NO-releasing compound. When more than one compound is administered to the patient, the compounds can be mixed together, or they can be administered to the patient sequentially. Any one, or a combination, of the following routes of administration can be used to administer the NO-releasing compound(s) to the patient: intravenous injection, intraarterial injection, transcutaneous delivery, oral delivery, and inhalation (e.g., of a gas, powder or liquid), although administration of both components by inhalation is preferred.

Particularly, in some embodiments, the NO-releasing compound is a pharmaceutically acceptable nitrite. "Nitrite" as used herein refers to the inorganic anion $^-NO_2$ or a salt of nitrous acid ($NO_2^-$). Nitrite anions are present in concentrations about 150-1000 nM in the plasma and about 10 $\mu$M in aortic tissue. Physiological mechanisms exist to reduce nitrite to nitric oxide (NO), and thus, nitrite has the properties as a vasodilator. Additional hemodynamic effects of nitrite in pulmonary hypertension can be found in U.S. Pat. Nos. 8,927,030 and 9,387,224, and Simon et al. "Acute hemodynamic effects of inhaled sodium nitrite in pulmonary hypertension associated with heart failure with preserved ejection fraction" *JCI Insight*. 2016; 1(18): e89620, which documents are hereby incorporated by reference in their entirety.

By way of non-limiting example, some pharmaceutically acceptable nitrites that are contemplated for use in connection with the present invention include nitrite salts formed with alkali metals, such as sodium nitrite ($NaNO_2$, also known as nitrous acid sodium salt), potassium and lithium, with alkali earth metals, such as calcium, magnesium and barium, with organic bases, such as amine bases, for example, dicyclohexylamine, pyridine, arginine, lysine and the like. Other nitrite salts may be formed from a variety of organic and inorganic bases. In particular embodiments, the nitrite is a salt of an anionic nitrite delivered with a cation, which cation is selected from sodium, potassium, and arginine. Many nitrite salts are commercially available, and/or readily produced using conventional techniques.

Particularly, in some embodiments, the pharmaceutically acceptable nitrite is sodium nitrite.

The term "therapeutically effective amount" as used herein refers to a quantity of compound sufficient to achieve a desired effect in a subject being treated. For example, an therapeutically effective amount of a therapeutic agent or drug for treating pulmonary hypertension may be the amount necessary to ameliorate or inhibit elevation of pulmonary arterial pressure over normal levels in the subject, and more particularly, the amount sufficient for maintaining one or more of the right atrial pressure, pulmonary capillary wedge pressure, right ventricular systolic and diastolic pressures, pulmonary artery systolic and diastolic pressures, filling pressure within the normal range, in the subject.

In some embodiments, multiple pharmaceutical agents are co-administered to the subject for treating the disease. The term "co-administer" or "co-administration" as used herein means that multiple therapeutic agents, such as a PDE5 inhibitor and a NO-releasing compound, are administered so that their respective effective periods of biological activity will overlap in the subject being treated. Co-administration can be carried out by contemporaneous or sequential administration of multiple therapeutic agents, for example, administering a second therapeutic agent before, during or after the administration of a first therapeutic agent.

In some embodiments, multiple pharmaceutical agents may be co-administered to improve in vivo effect of at least one pharmaceutical agent. For example, it has been shown that nitric oxide (NO) is a powerful vasodilator with a very short half-life in blood. In the present disclosure, it is contemplated that co-administration a NO-releasing compound and a PDE5 inhibitor can prevent premature breakdown or otherwise reduce the elimination rate of the administered NO-releasing compound in vivo. Accordingly, in some embodiments, a PDE5 inhibitor is administered at an amount sufficient to increase the half-life of a co-administered NO-releasing compound. Specifically, in some embodiments, the PDE5 inhibitor is administered at an amount sufficient to improve bioavailability of nitric oxide (NO) in the subject.

In one aspect of the present disclosure, it has been contemplated that therapeutically effective amounts of a PDE5 inhibitor and a NO-releasing compound, alone or in combination, can be administered by inhalation, without causing significant side effects, especially no significant side effects related to systemic blood pressure and circulation as well as no gas exchange deterioration or disruptions. Methods and devices for administering by inhalation therapeutic compositions containing PDE5 inhibitors for the treatment of pulmonary hypertension can be found in U.S. Pat. No. 9,238,240, which reference is herein incorporated by reference in its entirety.

"Administration by inhalation" in the present context refers to the delivery of the active ingredient or a combination of active ingredients through a respiratory passage of a subject in need of the active ingredient(s), such as the subject's nose or mouth.

Accordingly, provided are methods for treating a subject suffering from a condition associated with an elevated blood pressure, such as pulmonary hypertension, through the administration by inhalation a therapeutically effective amount of a PDE5 inhibitor, such as vardenafil or a pharmaceutically acceptable salt, N-oxide, ester, quaternary ammonium salt, hydrate or prodrug thereof. In some embodiments, the method further comprises administering to the subject a therapeutically effective amount of a NO-releasing compound, such as a pharmaceutically acceptable nitrite. Further in some embodiments, the PDE5 inhibitor and the NO-releasing compound are co-administered.

In some embodiments, administration by inhalation is performed through the use of an inhalation device, and preferably a compact inhalation device. Particularly, in some embodiments, the inhalation device controls the dose of drug to be administered. For example, in some embodiments, the inhalation device is a metered dose inhaler (MDI), capable of delivering a predetermined specific amount of respiratory drug, such as the therapeutic agents or drugs as disclosed herein, to the subject's lungs, during each session of administration. In some embodiments, a predetermined dose of pharmaceutical composition may be contained in the inhalation device or added to the inhalation device before using.

In some embodiments, pharmaceutical compositions are provided as a pressurized aerosol. In other embodiments, pharmaceutical compositions are provided in a liquid or solid formulation to be nebulized before administration. Accordingly, in some embodiments, the inhalation device further comprises a nebulizing mechanism that turns a pharmaceutical composition into a medical aerosol before administration.

As used herein, the term "medical aerosol" refers to a pharmaceutically acceptable colloid of fine solid particles or liquid droplets, in air or another gas, containing one or more pharmaceutical agents for treating a disease. Particularly, liquid aerosols comprising fine droplets of drug-containing solution and dry aerosols in the form of finely divided solid compound not dissolved or suspended in a liquid are contemplated as useful for the present disclosure. In some embodiments, medical aerosols according to the present disclosure comprise at least a PDE5 inhibitor and/or a NO-releasing compound. Particularly, in some embodiments, the PDE5 inhibitor is vardenafil or a pharmaceutically acceptable salt or ester thereof, such as vardenafil HCl; and the NO-releasing compound is a pharmaceutical acceptable nitrite, such as sodium nitrite. In some embodiments, the medical aerosol of the present disclosure is delivered by inhalation to a subject for the treatment of pulmonary hypertension.

In some embodiments, the inhalation device comprises a nebulizer, such as a jet nebulizer, a ultrasonic nebulizer, a vibration, a mesh nebulizer, which nebulizes a pharmaceutical composition in a liquid or solid formulation into a medical aerosol having suitable properties for treating certain diseases. For example, in some embodiments, the medical aerosol is generated from a pharmaceutical composition containing a respiratory drug for treating pulmonary hypertension in a subject. For a review of clinical nebulizers, see e.g., Ari A. "Jet, Ultrasonic, and Mesh Nebulizers: An Evaluation of Nebulizers for Better Clinical Outcomes," *Eurasian Journal of Pulmonology* 2014; 16: 1-7, which reference is incorporated herein by reference in its entirety.

In some embodiments, the inhalation device is a dry powder inhaler (DPI). In these embodiments, a solid formulation containing the respiratory drug is nebulized and inhaled in the form of fine powders. Particularly, in some embodiments, the aerosol particles are less than about 10 μm, or less than about 5 μm, or less than about 4 μm in diameter.

In some embodiments, the inhalation device is a soft mist inhaler (SMI). In these embodiments, a solution containing the respiratory drug is nebulized into an aerosol containing small droplets. Particularly, in some embodiments, the liquid pharmaceutical composition has a osmolality in the range of about 20 to about 2000 mOsmol/kg. In some embodiments, the pharmaceutical composition has a dynamic viscosity in the range of about 0.5 mPas to about 5 mPas. In some embodiments, the pharmaceutical composition exhibits a surface tension in the range of about 5 mN/m to about 100 mN/m.

In some embodiments, a medical aerosol can be generated by passing a pharmaceutical formulation containing the respiratory drug through a nozzle or series of nozzles. The aerosol generation can be achieved in SMI, for example, by mechanical, electromechanical or thermomechanical process. Examples of soft mist inhalers include the Respimat® Inhaler (Boeringer Ingelheim GmbH), the AERx®. Inhaler (Aradigm Corp.), the Mystic™ Inhaler (Ventaira Pharmaceuticals, Inc) and the Aira™ Inhaler (Chrysalis Technologies Incorporated). For a review of soft mist inhaler technology, see e.g. M. Hindle, The Drug Delivery Companies Report, *Autumn/Winter* 2004, pp. 31-34, which reference is herein incorporated by reference in its entirety. The aerosol for SMI can be generated from a solution of the respiratory drug further containing pharmaceutically acceptable excipients. In the present case, the respiratory drug is a PDE5 inhibitor, such as vardenafil, its derivative or a pharmaceutically acceptable salt or ester thereof, which can be formulated in SMI is as a solution. The respiratory drug alternatively or additionally further comprises a NO-releasing compound, such as nitrite or a pharmaceutically acceptable salt or ester thereof. The solution can be, for example, a solution of the one or more active ingredient(s) in water, ethanol or a mixture thereof.

Particularly, in some embodiments, distribution of the aerosol particle or droplet sizes maximizes deposition of the drug-containing particles or droplets in the subject's lungs after inhalation, thus optimizing the effect of the aerosol in treating pulmonary hypertension. For example, in some embodiments, the aerosol exhibit a mass median aerodynamic diameter (MMAD) of droplets or particles in the range of about 1 to about 10 μm and a geometric standard deviation (GSD) of less than 5. In some embodiments, aerosol exhibiting a fine particle fraction (FPF) that particles or droplets having a size less than about 5 μm in diameter are at least about 50%.

A therapeutically effective amount may be administered in a single dose, or in several doses during a course of treatment. The therapeutically effective amount will vary depending on the condition being treated, the severity thereof, physiological conditions of the patient to be treated, such as age, body weight, and route of administration, etc., The skilled artisan will be able to determine appropriate dosages depending on these and other factors.

Particularly, it is contemplated that administering the present pharmaceutical composition by inhalation in a single event can be carried out in a limited number of breaths by a subject. For example, a single dose can be administered in 20 breaths or less, or in 10 breaths or less, or than 5 breaths or less. Preferably, a dose is administered in 3, 2 or 1 breaths. The total time of a single administering event can be less than 5 minutes, or less than 1 minute, or less than 30 seconds. A pharmaceutical composition can be administered a single dose per day or several doses per day. Particularly, in some embodiments, the pharmaceutical composition comprises a PDE5 inhibitor and/or a NO-releasing compound. More particularly, in some embodiments, the PDE5 inhibitor is vardenafil or a pharmaceutically acceptable salt or ester thereof, such as vardenafil HCl, and the NO-releasing compound is a pharmaceutically acceptable nitrite, such as sodium nitrite.

A unit dose of a PDE5 inhibitor to be administered by inhalation in a single administration event can be from about 15 μg to about 100 μg or from about 15 μg to about 90 μg or from about 30 μg to about 90 μg or from about 30 μg to about 60 μg in a single administration event or a single dose. The unit dose of a NO-releasing compound to be administered by inhalation can be from about 15 μg to about 100 μg or from about 15 μg to about 90 μg or from about 30 μg to about 90 μg or from about 30 μg to about 60 μg in a single administration event or a single dose.

By way of example, as described herein, it is now contemplated that from about 0.001 to about 2 microgram per kilogram body weight; or from about 1 to about 500 μg per kilogram body weight of vardenafil or a pharmaceutically acceptable salt or ester thereof may be administered to a subject for treating pulmonary hypertension. Particularly, in some embodiments, no more than about 200 μg per kilogram body weight of vardenafil or a pharmaceutically acceptable salt or ester thereof may be administered; In some embodiments, no more than about 100 μg per kilogram body weight of vardenafil or a pharmaceutically acceptable salt or ester thereof may be administered; in some embodiments, no more than about 50 μg per kilogram body weight of vardenafil or a pharmaceutically acceptable salt or ester thereof may be administered; in some embodiments, no more than about 25 μg per kilogram body weight of vardenafil or a pharmaceutically acceptable salt or ester thereof may be administered.

Further, it is contemplated that a pharmaceutically acceptable nitrite may be administered or co-administered with a PDE5 inhibitor to a circulation concentration of about 0.5 μM to about 250 μM in the general circulation of the subject for treating pulmonary hypertension. Particularly, in some embodiments, the pharmaceutically acceptable nitrite is administered to a circulation concentration of no more than about 100 μM in the general circulation of the subject; in some embodiments, the pharmaceutically acceptable nitrite is administered to a circulation concentration of no more than about 20 μM in the general circulation of the subject; in some embodiments, the pharmaceutically acceptable nitrite is administered to a circulation concentration of no more than about 16 μM in the general circulation of the subject; in some embodiments, the pharmaceutically acceptable nitrite is administered to a circulation concentration of less than 16 μM in the general circulation of the subject.

In some embodiments, the PDE5 inhibitor and/or nitrite can be administered one, two, three, or four or more times a day. In some embodiments, the subject being treated administers the PDE5 inhibitor and/or nitrite as often as needed and in an amount needed to address symptoms of the pulmonary hypertension or other condition. In some embodiments, the subject being treated administers the PDE5 inhibitor and/or nitrite up to a maximum amounts of each. The maximum amounts of each can be determined by a health care provider, such as a physician, or determined based on tolerance of side effects. The delivery device, such as inhalation device, can be programmed to allow a maximum amount of drug to be administered in any period of time, such as a treatment session or 24-hour period.

Further in some embodiments, a method for treating pulmonary hypertension can further comprises administering or co-administering at least one supplementary therapeutic agent additional to the PDE5 inhibitors or NO-releasing compounds as described herein. By way of example, such supplementary therapeutic agent may be calcium channel blockers (diltiazem, amlodipine, nifedipine), bosentan, sitaxsentan, ambrisentan, and pharmaceutically acceptable salts thereof. In some embodiments, supplementary therapeutic agents may be pain relievers, anti-inflammatory agents, antihistamines, and the like. Bu way of examples, such supplementary therapeutic agents may be one or more of penicillin, hydroxyurea, butyrate, clotrimazole, and arginine.

In some embodiments, the supplementary therapeutic agents can be included in the same formulation as the PDE5 inhibitors and/or NO-releasing compounds and, thus, can be administered simultaneously using a inhalation device. In some embodiments, the supplementary therapeutic agents can be administered separately by inhalation or using a different administration route. In some embodiments, the application of intravenous prostacyclin (flolan), intravenous iloprost or intravenous or subcutaneous treprostinil can be administered in addition to vardenafil and/or nitrite sodium administered via inhalation using a metered dose inhaler.

In another aspect of the present disclosure, provided herein are pharmaceutical compositions to be used with the present methods. Particularly, disclosed herein are pharmaceutical compositions for treating a condition associated with elevated blood pressure or decreased blood flow in a subject, including those associated with elevated blood pressure in the lungs, such as pulmonary hypertension. In some embodiment, this includes treating a subject suffering from neonatal pulmonary hypertension. In other embodiments, this includes treating a subject suffering from primary and/or secondary pulmonary hypertension. In various embodiments, the present composition may also be used alone or in combination with additional other therapies for the treatment of vasospasm, stroke, angina, ischemia, revascularization of coronary arteries and other arteries (peripheral vascular disease), transplantation (e.g., of kidney, heart, lung, or liver), treatment of low blood pressure (such as that seen in shock or trauma, surgery and cardiopulmonary arrest) to prevent reperfusion injury to vital organs, cutaneous ulcers (e.g., with topical, non-acidified nitrite salt), Reynaud's phenomenon, treatment of hemolytic conditions (such as sickle cell, malaria, TTP, and HUS), hemolysis caused by immune incompatibility before and after birth, and other conditions.

In some embodiments, the present pharmaceutical compositions comprise at least one PDE5 inhibitor, at least one NO-releasing compound and pharmaceutically acceptable carriers. The PDE5 inhibitor and the NO-releasing compound can be any such compounds as disclosed herein. Particularly, in some embodiments, the PDE5 inhibitor is vardenafil or a pharmaceutically acceptable salt of ester thereof, such as vardenafil HCl. In some embodiments, the NO-releasing compound is a pharmaceutically acceptable nitrite, such as sodium nitrite.

In some embodiments, the pharmaceutical composition is nebulized and suitable for administration by inhalation to the subject. Particularly, in some embodiments, the pharmaceutical composition is medical aerosol containing pharmaceutical agents or drugs for treating pulmonary hypertension. Particularly, the aerosol exhibits aerodynamic properties suitable for deposing the particles or droplets in certain portion of a subject's respiratory passage for treating pulmonary hypertension, such as in the lungs. More particularly, in some embodiments, the aerosol exhibits a mass median aerodynamic diameter (MMAD) of droplets or particles in the range of about 1 to about 10 μm and a geometric standard deviation (GSD) of less than 5. In some embodiments, aerosol exhibiting a fine particle fraction (FPF) in particles or droplets having a size less than about 5 μm of at least about 50%.

In other embodiments, the pharmaceutical composition is a dry powder. Particularly, in some embodiments, the powders have an average particle size of less than about 10 μm, or less than about 5 μm, or less than about 4 μm. In yet other embodiments, the pharmaceutical composition is a solution. Particularly, the solution has an osmolality in the range of about 20 to about 2000 mOsmol/kg. In some embodiments, the pharmaceutical composition has a dynamic viscosity in the range of about 0.5 mPas to about 5 mPas. In some embodiments, the pharmaceutical composition exhibits a surface tension in the range of about 5 mN/m to about 100 mN/m.

By way of example, as described herein, it is now contemplated that a concentration of a PDE5 inhibitor in a pharmaceutical composition (such as a solution) to be administered by inhalation can range from about 200 μg/ml to about 2500 μg/ml; or from about 200 μg/ml to about 10000 μg/ml; or from about 500 μg/ml to about 2500 μg/ml, or from about 800 μg/ml to about 2200 μg/ml, or from about 1000 μg/ml to about 2000 μg/ml.

Additionally or alternatively, the pharmaceutical composition to be administered by inhalation can further contain a NO-releasing compound. By way of example, as described herein, it is now contemplated that a concentration of a NO-releasing compound in the pharmaceutical composition can range from about 200 μg/ml to about 2500 μg/ml; or from about 200 μg/ml to about 10000 μg/ml; or from about 500 μg/ml to about 2500 μg/ml, or from about 800 μg/ml to about 2200 μg/ml, or from about 1000 μg/ml to about 2000 μg/ml.

Further, in some embodiments, the pharmaceutical composition may contain one or more unit doses, such as in separate containers, capsules or cartridges, each to be administered in a single administration event. By way of examples, it is now contemplated that a single dose of the composition may comprise a PDE5 inhibitor of about 15 μg to about 100 μg or from about 15 μg to about 90 μg or from about 30 μg to about 90 μg or from about 30 μg to about 60 μg. A single dose of the composition may comprise a NO-releasing compound of about 15 μg to about 100 μg or from about 15 μg to about 90 μg or from about 30 μg to about 60 μg. Particularly, in some embodiments, the PDE5 inhibitor is vardenafil or a pharmaceutically acceptable salt or ester thereof, such as vardenafil HCl, while the NO-releasing compound is a pharmaceutically acceptable nitrite, such as sodium nitrite.

The pharmaceutically acceptable carrier useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of the compounds herein disclosed.

In general, the nature of carrier depends on the particular mode of administration being employed. For instance, solid aerosols may contain a solid particulate carrier which generally is a non-toxic material chemically inert to the inhalation medicament but may, if so desired, also comprises larger particles of the inhalation medicament. Particularly, in some embodiments, the drug particles are packaged in larger porous particles of a carrier material, such as solid lipidic particles, such as those disclosed in U.S. Patent Application No. 20100119587, which document is herein incorporated by reference in its entirety.

In some embodiments, carrier particles are used to improve drug particle flowability, thus improving dosing accuracy and minimizing dose variability observed with drug formulations alone. In some embodiments, carrier particles help drug particles emit more easily from the inhalation device, thus improving inhalation efficiency. In some embodiments, when the bulk of drug particles to be administered is small, carrier particles serve to provide bulk, thus improving the handling, dispensing and metering of the drug administration. In some embodiments, the presence of a carrier material improves the taste or sensation on inhalation. Examples of carriers which may be used in the composition include a sorbitol, dextran, mannitol and, preferably, lactose, such as crystalline lactose. Additional suitable types and properties of carriers for dry power inhalation composition can be found in Hamed Hamishehkar, Yahya Rahimpour and Yousef Javadzadeh (2012). The Role of Carrier in Dry Powder Inhaler, Recent Advances in Novel Drug Carrier Systems, PhD. Ali Demir Sezer (Ed.), InTech, DOI: 10.5772/51209, which reference is herein incorporated by reference in its entirety.

In some embodiments, liquid formulations may comprise pharmaceutically and physiologically acceptable fluids such as water, physiological saline, balanced salt solutions, aqueous dextrose, glycerol or the like as a vehicle. Liquid formulations to be nebulized before administration by inhalation may comprise a solvent for one or more pharmaceutical agents, osmolality adjusting agents, or surfactants, etc. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In yet another aspect of the present disclosure, provided herein are kits of parts to be used with the present methods. Particularly, provide herein are kits that include a inhalation device and a pharmaceutical composition as described herein. In some embodiments, the inhalation device contains the pharmaceutical composition. In some embodiments, the pharmaceutical composition is in a formulation readily to be administered by inhalation, such as a pressurized aerosol. In some embodiments, the inhalation device is configured to nebulize the pharmaceutical composition into an aerosol before administration.

Particularly, in some embodiment, the inhalation device is a pressurized pack with a dispensing nozzle. In other embodiments, the inhalation device comprises a nebulizer. In some embodiments, the inhalation device is a metered dose inhaler, a pulsed nebulizer that nebulizes a fixed amount of the pharmaceutical composition per pulse, a dry powder inhaler or a soft mist inhaler.

In some embodiments, the pharmaceutical composition is in a solid form, and particularly as a dry powder having an average particle size of less than about 10 μm, or less than about 5 μm or less than about 4 μm. In some embodiments, the pharmaceutical composition is in a liquid formulation, such as a solution of one or more pharmaceutical agents in a suitable solvent, such as water, ethanol or a mixture thereof.

In some embodiments, the pharmaceutical composition comprises at least one PDE5 inhibitor and/or at least one NO-releasing compound. Particularly, in some embodiments, the PDE5 inhibitor is vardenafil or a pharmaceutically acceptable salt or ester thereof, such as vardenafil HCl. In some embodiments, the NO-releasing compound is a pharmaceutically acceptable nitrite, such as sodium nitrite.

In some embodiments, the kit further comprises individual unit doses of the pharmaceutical composition in separate compartment, each unit dose contains an amount for a single administration event. In some embodiments, the kit comprises multiple different pharmaceutical compositions, containing different pharmaceutical agents or drugs as active ingredients. For example, in some embodiments, the kit comprises a first composition containing the NO-releasing compounds and a second composition containing the PDE5 inhibitor.

In some embodiments, the kit further comprises instructions for use. Such instructions include but are not limited to instructions on the pharmaceutical effects, intended use, dosage information, and side effects of compositions provided with the kit; instructions on how to operate the inhalation device; and instructions on how to coordinate a patient's breathing and actuation of the inhaler. Particularly, in some embodiments, the instructions are drawn to the use of the kit for treatment of pulmonary hypertension, such as identification of specific symptoms associated with pulmonary hypertension, and those can be treated with the use of the kit.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above.

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

All patents, patent applications, provisional applications, and publications referred to or cited herein are incorporated by reference in their entirety, including all figures and tables, to the extent they are not inconsistent with the explicit teachings of this specification

What is claimed is:

1. A method for extending the half-life or reducing the in vivo elimination rate of an NO-releasing compound following its administration to a subject in need of such treatment, comprising administering to the subject a phosphodiesterase type-5 inhibitor and an NO-releasing compound, wherein the phosphodiesterase type-5 inhibitor is administered in an amount sufficient to extend the half-life or reduce the in vivo elimination rate of the NO-releasing compound in blood of the subject, wherein no more than about 25 μg per kilogram body weight of the PDE-5 inhibitor is administered, wherein the NO-releasing compound is sodium nitrite, wherein the sodium nitrite is administered to achieve a circulating concentration of 16 to 250 μM nitrite anion and wherein said administering to the subject produces an amount of NO in the subject effective to decrease the pulmonary arterial pressure of the subject, wherein the phosphodiesterase type-5 inhibitor is vardenafil or a pharmaceutically acceptable salt thereof, wherein vardenafil is administered in a dosage of about 0.0001 to about 2 μg per kilogram body weight and wherein a dose of the sodium nitrite is from about 15 μg to about 100 μg.

2. The method according to claim 1, wherein the phosphodiesterase type-5 inhibitor and the NO-releasing compound are administered in separate compositions, simultaneously or sequentially.

3. The method according to claim 1, wherein the phosphodiesterase type-5 inhibitor and the NO-releasing compound are co-administered.

4. The method according to claim 1, wherein one or both of the phosphodiesterase type-5 inhibitor and the NO-releasing compound are formulated as a pharmaceutical composition adapted for nebulization into liquid or dry powder medical aerosols for delivery by inhalation to the subject.

5. The method according to claim 4, wherein the pharmaceutical composition is administered to the subject with a metered dose inhaler capable of delivering a fixed amount of the pharmaceutical composition per pulse.

6. The method according to claim 1, wherein the subject is a human.

7. The method according to claim 1, wherein the subject suffers from pulmonary hypertension.

8. The method according to claim 5, wherein the metered dose inhaler is a dry powder inhaler or a soft mist inhaler.

9. A method for extending the half-life or reducing the in vivo elimination rate of an NO-releasing compound following its administration to a subject in need of such treatment, comprising administering to the subject a phosphodiesterase type-5 inhibitor and an NO-releasing compound, wherein the phosphodiesterase type-5 inhibitor is administered in an amount sufficient to extend the half-life or reduce the in vivo elimination rate of the NO-releasing compound in blood of the subject, wherein no more than about 25 μg per kilogram body weight of the PDE-5 inhibitor is administered, wherein the NO-releasing compound is sodium nitrite, wherein the sodium nitrite is administered to achieve a circulating concentration of 100 to 250 μM nitrite anion and wherein said administering to the subject produces an amount of NO in the subject effective to decrease the pulmonary arterial pressure of the subject.

10. The method according to claim 9, wherein the phosphodiesterase type-5 inhibitor and the NO-releasing compound are administered in separate compositions, simultaneously or sequentially.

11. The method according to claim 9, wherein the phosphodiesterase type-5 inhibitor and the NO-releasing compound are co-administered.

12. The method according to claim 9, wherein one or both of the phosphodiesterase type-5 inhibitor and the NO-releasing compound are formulated as a pharmaceutical composition adapted for nebulization into liquid or dry powder medical aerosols for delivery by inhalation to the subject.

13. The method according to claim 12, wherein the pharmaceutical composition is administered to the subject with a metered dose inhaler capable of delivering a fixed amount of the pharmaceutical composition per pulse.

14. The method according to claim 9, wherein the subject is a human.

15. The method according to claim 9, wherein the phosphodiesterase type-5 inhibitor is vardenafil or a pharmaceutically acceptable salt thereof.

16. The method according to claim 15, wherein vardenafil is administered in a dosage of about 0.0001 to about 2 μg per kilogram body weight.

17. The method according to claim 9, wherein the subject suffers from pulmonary hypertension.

18. The method according to claim 13, wherein the metered dose inhaler is a dry powder inhaler or a soft mist inhaler.

* * * * *